US010172625B2

(12) United States Patent
Wada et al.

(10) Patent No.: US 10,172,625 B2
(45) Date of Patent: Jan. 8, 2019

(54) HEMOSTATIC INSTRUMENT

(71) Applicant: TERUMO KABUSHIKI KAISHA, Shibuya-ku, Tokyo (JP)

(72) Inventors: Satoshi Wada, Shizuoka (JP); Daisuke Nakashima, Shizuoka (JP); Tatsuya Ouchi, Shizuoka (JP); Masako Aramiya, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 213 days.

(21) Appl. No.: 15/369,051

(22) Filed: Dec. 5, 2016

(65) Prior Publication Data
US 2017/0086855 A1    Mar. 30, 2017

Related U.S. Application Data
(63) Continuation of application No. PCT/JP2015/067878, filed on Jun. 22, 2015.

(30) Foreign Application Priority Data

Jun. 27, 2014   (JP) ................................. 2014-132683

(51) Int. Cl.
*A61B 17/135*   (2006.01)
*A61M 5/00*    (2006.01)
(Continued)

(52) U.S. Cl.
CPC ........ *A61B 17/1355* (2013.01); *A61B 17/135* (2013.01); *A61M 5/00* (2013.01);
(Continued)

(58) Field of Classification Search
CPC .............. A61B 17/135; A61B 17/1325; A61B 17/132; A61B 17/1355;
(Continued)

(56) References Cited

U.S. PATENT DOCUMENTS 5,433,724 A * 7/1995 Kawasaki .......... A61B 17/1325
                                                    600/499
5,464,420 A * 11/1995 Hori .................... A61B 17/1325
                                                    606/202
(Continued)

FOREIGN PATENT DOCUMENTS

GB        1 206 605 A     9/1970
JP      47-011907 Y2     6/1972
(Continued)

OTHER PUBLICATIONS

International Search Report (PCT/ISA/210) dated Aug. 25, 2015, by the Japanese Patent Office as the International Searching Authority for International Application No. PCT/JP2015/067878.
(Continued)

*Primary Examiner* — Katrina Stransky
(74) *Attorney, Agent, or Firm* — Buchanan Ingersoll & Rooney PC

(57) ABSTRACT

A pressure adjustment unit of a hemostatic instrument includes a main container portion connected to a side of a balloon and an auxiliary balloon serving as an expansion member. The main container portion has, for example, air passing holes for permitting a portion of a fluid (air) to be expelled. A sliding member is installed at the main container portion and is movable along the main container portion from a state in which the air passing holes of the main container portion are blocked to a state in which one or more of the hole are open, and a moving body movable inside the main container portion to successively block the air passing holes opened by moving the sliding member.

19 Claims, 6 Drawing Sheets

(51) Int. Cl.
*A61B 17/00* (2006.01)
*A61B 90/00* (2016.01)

(52) U.S. Cl.
CPC ............... *A61B 2017/00455* (2013.01); *A61B 2017/00876* (2013.01); *A61B 2090/032* (2016.02); *A61B 2090/0807* (2016.02)

(58) Field of Classification Search
CPC ........... A61B 2017/00455; A61B 2017/00876; A61B 2090/032; A61B 2090/0807; A61M 5/00; A61M 39/00; A61F 5/34; A61F 5/32; B60C 29/00
See application file for complete search history.

(56) References Cited

U.S. PATENT DOCUMENTS

| | | | |
|---|---|---|---|
| 5,792,173 A | 8/1998 | Breen et al. | |
| 2003/0167070 A1* | 9/2003 | McEwen | A61B 17/135 606/203 |
| 2004/0098035 A1* | 5/2004 | Wada | A61B 17/1325 606/201 |
| 2004/0122469 A1* | 6/2004 | Akerfeldt | A61B 17/1325 606/201 |
| 2004/0147956 A1* | 7/2004 | Hovanes | A61B 5/02208 606/202 |
| 2007/0191881 A1 | 8/2007 | Amisar et al. | |
| 2012/0041476 A1* | 2/2012 | Lin | A61B 17/1355 606/202 |
| 2013/0023734 A1* | 1/2013 | Okamura | A61B 17/1325 600/227 |
| 2013/0085524 A1* | 4/2013 | Dahlberg | A61B 17/1325 606/202 |
| 2014/0228732 A1* | 8/2014 | Steinbaugh | A61B 17/135 602/53 |
| 2014/0236058 A1* | 8/2014 | Lee | A61B 17/1355 601/84 |

FOREIGN PATENT DOCUMENTS

| | | |
|---|---|---|
| JP | 47-031484 A | 11/1972 |
| JP | 61-018110 U | 2/1986 |
| JP | 7-079983 A | 3/1995 |
| JP | 2000-515773 A | 11/2000 |
| JP | 2004-201829 A | 7/2004 |

OTHER PUBLICATIONS

Written Opinion (PCT/ISA/237) dated Aug. 25, 2015, by the Japanese Patent Office as the International Searching Authority for International Application No. PCT/JP2015/067878.

* cited by examiner

HEMOSTATIC INSTRUMENT

CROSS-REFERENCES TO RELATED APPLICATIONS

This application is a continuation of International Application No. PCT/JP2015/067878 filed on Jun. 22, 2015, and claims priority to Japanese Patent Application No. 2014-132683 filed on Jun. 27, 2014, the entire content of both of which is incorporated herein by reference.

TECHNICAL FIELD

The present invention relates to a hemostatic instrument that stops bleeding by pressing a puncture site such as an arm.

BACKGROUND ART

An operator may provide treatment or perform a test by percutaneously inserting a catheter or a similar medical device into a lesion area (e.g., a blood vessel) of a living body through the lumen of an introducer sheath. The introducer sheath is introduced to the living body through a puncture site of an arm or a leg corresponding to a limb of a patient. When the introducer sheath is removed from the living body, bleeding needs to be stopped at the puncture site.

An air injection type pressing hemostatic instrument may be used to stop bleeding at the puncture site.

A band body of the hemostatic instrument is wound and fixed around the puncture site formed in the arm or the leg to inject air from a syringe or a similar medical device into a balloon of the band body. The balloon thus expands and exerts a pressure force on the puncture site.

Over time, however, a hole of the blood vessel may be blocked by a blood clot or the like. Thus, when pressing is performed by the hemostatic instrument at a constant pressure force, blood flow in the blood vessel may be hindered, or numbness or pain may be caused. In this regard, in a hemostatic instrument disclosed in Japanese Patent Application Publication No. JP-A-2004-201829, a pressure force of a balloon may be naturally relieved over time without an operation of an operator after the balloon is dilated.

SUMMARY

In the above-described conventional hemostatic instrument, the pressure force exerted by the balloon is naturally relieved over time without any further operation by an operator after the balloon is dilated. Thus, the operator cannot decide to adjust the pressure force in response to a state of a patient from when the balloon is dilated and bleeding begins to be stopped until the bleeding is stopped.

The hemostatic instrument disclosed in this application allows an operator to easily adjust the pressure force to a region of a limb in which bleeding needs to be stopped in response to the state of the patient when the region is pressed. The hemostatic instrument of this application can further reduce the effort required by the operator to adjust the pressure force.

A hemostatic instrument disclosed in this application includes a band body wound and fixed around a region of a limb in which bleeding is to be stopped, an expansion member connected to the band body and expanded when a fluid is injected to apply a pressure force for stopping bleeding in the region to the region, a connector provided in an end portion of an injection passage for injecting the fluid into the expansion member, and a pressure adjustment unit that adjusts a pressure of the expansion member. Herein, the pressure adjustment unit includes a main container portion connected to communicate with the expansion member, the main container portion having a fluid passing hole for extracting a portion of the fluid, a sliding member installed in the main container portion and moved along the main container portion from a state in which the fluid passing hole of the main container portion is blocked to open the fluid passing hole, and a moving body movable inside the main container portion at a position at which the fluid passing hole is blocked and a position at which the fluid passing hole is not blocked. The main container portion includes a communication port for communication with the expansion member, and a force applying means that applies a force that directs the moving body to a side at which the communication port is provided.

According to the above-described configuration, the force applying means applies a force to the moving body inside the main container portion to direct the moving body to the communication port side. For this reason, when the operator opens the fluid passing hole of the main container portion to reduce an internal pressure inside the expansion member, an internal pressure of a space formed between the moving body inside the main container portion and the communication port is reduced. Thus, the moving body moves toward the communication port side by the force applying means. The moving body inside the main container portion moves to the other end portion side of the main container portion until the opened fluid passing hole is blocked. Therefore, the operator may open the fluid passing hole of the main container portion to release a portion of the fluid of the expansion member by simply sliding the sliding member with respect to the main container portion. The operator may adjust the pressure force caused by the expansion member and applied to the region in which bleeding is to be stopped. This configuration allows the operator to easily arbitrarily adjust the pressure force applied to the region in which bleeding is to be stopped in response to a state of the patient, and an effort of the operator to adjust the pressure force may be reduced.

In this specification, the "fluid" includes liquid in addition to gas.

The "force applying means" may be a means for applying a force for directing the moving body to the communication port side inside the main container portion. For example, the force applying means may be a means that connects the moving body to the main container portion to apply a force to the moving body using an elastic force, and the like, or may be a means that applies a force to the moving body using a magnetic force, and the like, in a state in which the moving body is not connected to the main container portion.

In one embodiment, the force applying means corresponds to a first magnet and a second magnet. The first magnet is disposed in the main container portion, and the second magnet is disposed in the moving body.

According to the above-described configuration, the force applying means may apply a force to the moving body to direct the moving body to the side at which the communication port is provided using magnetic force acting between the first magnet and the second magnet.

The "magnet" includes not only a "permanent magnet" but also an "electromagnet".

In one embodiment, a repulsive force acts between the first magnet and the second magnet. Specifically, the main container portion has one end portion and the other end portion. The communication port for communication with the expansion member is provided in the other end portion, and the first magnet is provided in the one end portion. A repulsive force acts between the first magnet and the second magnet.

According to the above-described configuration, a force at which a space (first space) formed between the moving body inside the main container and the one end portion of the main container portion acts on the moving body (a force at which the force applying means acts on the moving body) may be set by the repulsive force acting between the first magnet and the second magnet. This configuration makes it possible to prevent an unnecessary force to inject the fluid into the expansion member from being applied when the operator expands the expansion member. For example, when an internal pressure forming the first space is set by an attractive force, since the operator detaches the first magnet and the second magnet, there is a concern that a greater force than necessary to inject the fluid into the expansion member may be applied. Hereinafter, a first space formed by the moving body inside the main container portion and the one end portion of the main container portion, and a second space formed by the moving body inside the main container portion and the other end portion of the main container portion are set.

Each of the first magnet and the second magnet may be made of a hard magnetic material, and a surface of the first magnet on the moving body side and a surface of the second magnet on the first end portion side correspond to the same magnetic pole.

According to the above-described configuration, the repulsive force is easily applied between the first magnet and the second magnet only by disposing a magnet such as a permanent magnet as described above.

In addition, a magnet or a permanent magnet corresponding to the hard magnetic material has a magnetic force without requiring an external energy supply, and thus the pressure adjustment unit may be easily configured. In addition, the hard magnetic material does not use an energy supply member to generate a magnetic field. The hard magnetic material is thus preferable in terms of miniaturization of the hemostatic instrument (i.e., volume reduction) and/or cost reduction.

The force applying means may also be a spring member. The spring member is disposed between the main container portion and the moving body.

When the force applying means is a spring member, the force applying means may apply a force to the moving body to direct the moving body to the side at which the communication port is provided using an elastic force caused by expansion and contraction of the spring member.

The "spring member" is a member that has an elastic force and is a member that has a property to return to a shape formed before a force is applied (natural state) when the force is applied. For this reason, the spring member may represent a magnitude of a force applied to the spring member using a magnitude of expansion and contraction of the spring member. For example, the spring member may be a coil spring or a flat spring.

The main container portion may have one end portion and the other end portion. The communication port for communication with the expansion member is provided at the other end portion, and the spring member is disposed between the one end portion and the moving body. The communication port and the spring member are thus at opposite ends of the main container portion.

When the expansion member is pressed, an internal pressure of the second space inside the main container portion rises, and the moving body moves to an opposite side from the communication port (the other end portion side of the main container portion). Thus, the spring member is compressed (i.e., shrinks) between the moving body and the one end portion. When the fluid passing hole of the main container portion is opened to reduce an internal pressure of the first space, a force for returning to a shape in a natural state formed before compression by the internal pressure of the second space acts on the spring member, and a force for directing the moving body to the side at which the communication port is provided is applied to the moving body. It is thus possible to have a configuration in which no more load than necessary to inject the fluid into the expansion member is applied when the operator expands the expansion member. In addition, since the communication port is not present in the other end portion of the main container portion, there is no concern that the spring member may block the communication port, and the spring member may be easily connected to the main container portion.

In one embodiment, the spring member connects the main container portion to the moving body.

According to the above-described configuration, the spring member corresponding to the force applying means may efficiently apply a force to the moving body to direct the moving body to the side at which the communication port is provided.

In one embodiment, the main container portion has one end portion and an other end portion opposite to the one end portion. The one end portion and the other end portion have retaining inhibition portions that inhibit the sliding member from slipping from the main container portion.

According to the above-described configuration, the sliding member may be prevented from slipping from the main container portion.

The hemostatic instrument disclosed here may allow an operator to easily adjust a pressure force to a region of a limb in which bleeding needs to be stopped in response to a state of a patient when the region is pressed, and the hemostatic instrument may reduce the effort necessary by the operator to adjust the pressure force.

According to another aspect, a hemostatic instrument comprises: a flexible band configured to be wound around a region of a limb of a living body that includes a bleeding puncture site; an inflatable member provided on an inner peripheral side of the flexible band that will face toward the limb during use of the hemostatic instrument, wherein the inflatable member is configured to expand when fluid is injected into an interior of the inflatable member, and the inflatable member is positioned to apply a pressure force to the region of the limb to stop the bleeding of the puncture site in the region of the limb when the inflatable member is expanded. An injection tube possesses a distal end and a proximal end, with the distal end of the injection tube being connected to the inflatable member, and the injection tube allowing the fluid to flow into the inflatable member. A first connector possesses a distal end and a proximal end, with the distal end of the connector communicating with the injection tube and the inflatable member, and the proximal end of the connector being configured to connect to a fluid injection device to introduce fluid into the injection tube and into the inflatable member. A pressure adjustment unit is connected to the injection tube and communicates with the injection tube and the inflatable member. The pressure adjustment unit includes a main container portion possessing an interior and an outer circumferential surface, with the main container portion comprising a plurality of through holes communicating the interior of the main container portion with outside environment to allow a portion of the fluid in the inflatable portion to be released to the outside environment by way of the main container portion. The main container portion also comprises a communication port opening into the interior of the main communication portion and communicating with the interior of the inflatable member by way of the injection tube. The pressure adjustment unit also includes a sliding member mounted on the outer circumferential surface of the main container portion and a movable body positioned in the interior of the main container portion. The sliding member is movable relative to the main container portion from a closed position in which the sliding member covers all of the through holes to a first open position in which one of the through holes is not covered by the sliding member to allow the portion of the fluid in the inflatable portion to be released through the one through hole to the outside environment. The movable body is positionable in one position in which the movable body is spaced from all of the through holes so that the movable body does not axially overlap any of the through holes, and is movable from the one position to an other position in which the movable body axially overlaps one of the through holes to prevent fluid in the interior of the main container body to flow through the one through hole to the outside environment.

In accordance with another aspect, a method comprises: attaching a hemostatic instrument to a puncture site of a limb of a living body, wherein the hemostatic instrument comprises a band and an inflatable body, with the inflatable body possessing an interior. The attaching of the hemostatic instrument to the puncture site of the limb of the living body involves winding the band around the limb of the living body so that the inflatable body is positioned between the band and the puncture site. The method additionally includes injecting a fluid into the interior of the inflatable body after the attaching of the hemostatic instrument to the puncture site of the limb to expand the inflatable body and apply pressure to the puncture site of the limb to assist in stopping bleeding. The interior of the inflatable body is in fluid communication with the interior of a main body, and the main body includes a plurality of through holes communicating the interior of the main body with outside environment. The main body also includes a sliding member mounted on the main body and a movable member movably positioned in the interior of the main body. The method also comprises reducing pressure within the inflatable body by moving the sliding member relative to the main body from a position in which the sliding member covers all of the through holes to a position in which one of the through holes is not covered by the sliding member and while the movable member is spaced from the one through hole so that fluid in the interior of the main body flows through the one through hole to outside environment, and automatically moving the movable member in the interior of the main body after reducing the pressure within the interior of the inflatable body so that the movable member blocks the one through hole.

DETAILED DESCRIPTION

Set forth below is a detailed description of embodiments with reference to the drawings of a hemostatic instrument and a method for using a hemostatic instrument representing examples of the inventive hemostatic instrument and method disclosed here.

Embodiments described below are suitable and specific examples of the hemostatic instrument, and thus some of the technically preferred aspects are detailed. However, the scope of the invention is not restricted to these aspects unless there is a description that restricts the invention in description below.

First Embodiment

Figure 1:
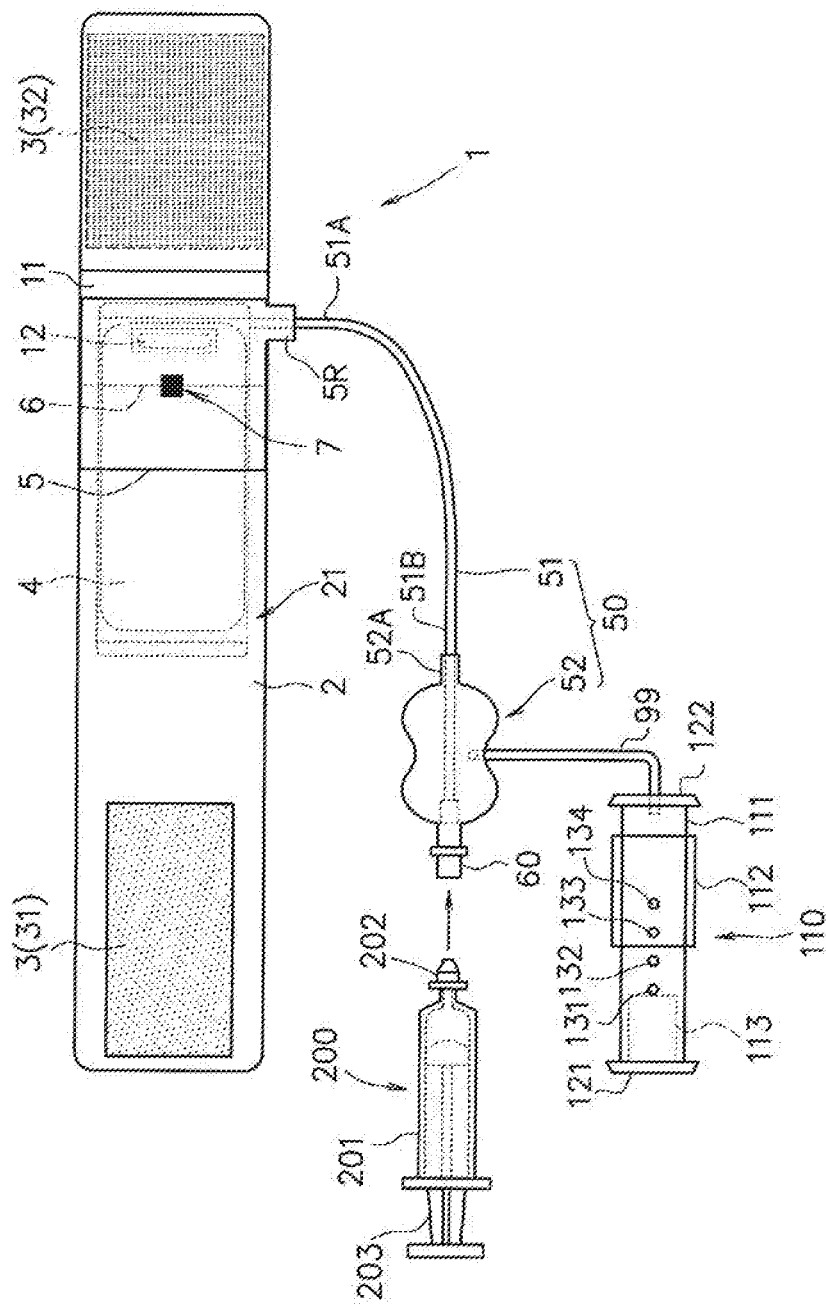
FIG. 1 illustrates a first embodiment of a hemostatic instrument, and shows an inner surface side of a band body (a surface side touching a skin) when this hemostatic instrument is installed, for example, on a wrist of a patient.
Figure 2:
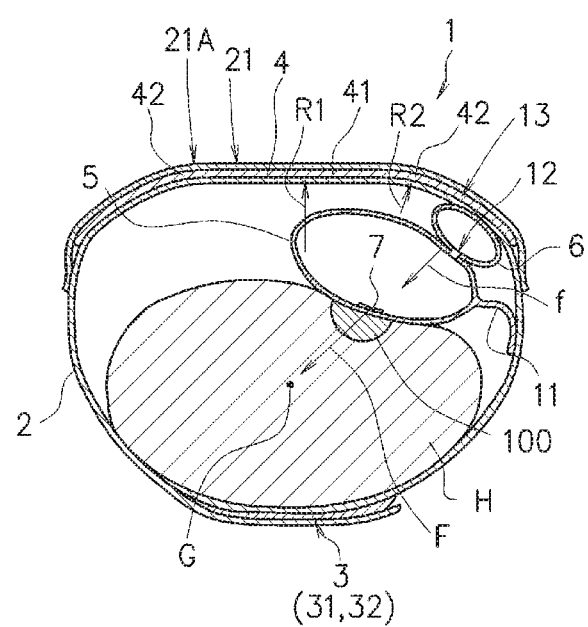
FIG. 2 is a cross-sectional view illustrating the hemostatic instrument shown in FIG. 1 being wound and installed around the wrist.

FIG. 1 illustrates a first embodiment of a hemostatic instrument. FIG. 1 is a diagram illustrating a surface corresponding to an inner surface side of a band body 2 (a surface side touching the skin of a patient) when this hemostatic instrument 1 is installed in a region of a limb of a patient in which bleeding needs to be stopped, for example, a wrist. FIG. 2 is a cross-sectional view illustrating a state in which the hemostatic instrument 1 illustrated in FIG. 1 is wound around and mounted on a wrist H.

As illustrated in FIG. 2, the hemostatic instrument 1 is wound around the wrist H corresponding to the region of the limb of the patient in which bleeding needs to be stopped. The hemostatic instrument is pressed against a puncture site 100 formed on the wrist H, thereby stopping the bleeding. The puncture site 100 is formed on the wrist H in order to insert a catheter or similar medical device into the living body to provide treatment or perform a test within a blood vessel. The hemostatic instrument 1 presses the puncture site 100 to stop bleeding after an introducer sheath indwelled in the puncture site 100 is removed.

The hemostatic instrument 1 includes a band body 2 to be wound around the wrist H, a hook and loop fastener 3, a reinforcing plate 4, a balloon 5 (e.g., an expansion member), an auxiliary balloon 6 (e.g., an expansion member), a marker 7, a pressure adjustment unit 110, and a syringe 200. The hook and loop fastener 3 is a fixing means for detachably fixing the band body 2 while the band body 2 is wound around the wrist H. The balloon 5 and the auxiliary balloon 6 dilate when air is fed into the balloon 5 and the auxiliary balloon 6.

The band body 2 is a belt-shaped member having flexibility (a flexible band). As illustrated in FIG. 2, the band body 2 is wound around the wrist H so that the band body 2 circles an outer circumference of the wrist H. An overlapping portion of the band body 2 is detachably fixed by the hook and loop fastener 3 (described below) to maintain a state in which the band body 2 is wound around the wrist H.

The material of the band body 2 is not particularly restricted as long as the operator may visually recognize the puncture site 100 through the band body 2. Examples of the constituent material of the band body 2 include various thermoplastic elastomers such as polyvinyl chloride, polyethylene, polypropylene, polybutadiene, polyolefin such as ethylene vinyl acetate copolymer (EVA), polyethylene terephthalate (PET), polyester such as polybutylene terephthalate (PBT), polyvinylidene chloride, silicone, polyurethane, polyimide elastomer, polyurethane elastomer, and polyester elastomer, or an arbitrary combination of these materials (e.g., a blend resin, a polymer alloy, a stacked body, and the like).

It is preferable that the band body 2 be substantially transparent. A transparent band body 2 may allow the operator to reliably visually recognize the puncture site 100 from the outside through the band body 2 (i.e., when viewing from external to the band body 2). This allows the operator to more easily position the marker 7 (described below) with respect to the puncture site 100. The band body 2 may thus be correctly positioned with respect to the wrist H.

As illustrated in FIG. 1 and FIG. 2, a reinforcing plate holder 21 (described below) is formed in a central part of the band body 2. The reinforcing plate holder 21 functions to accommodate and hold the reinforcing plate 4 (described below). A separate band body member 21A is joined to an outer surface side of the band body 2 (or the inner surface side of the band body 2) by an attachment method such as welding (heat welding, high-frequency welding, ultrasound welding, and the like) or adhesion (adhesion using an adhesive or a solvent). Therefore, the reinforcing plate holder 21 is doubly configured by the band body 2 and the separate band body member 21A (i.e., the band body 2 and the separate band body 21A collectively define the reinforcing plate holder 21). The reinforcing plate 4 is thus reliably held without moving by being inserted into a gap between the band body 2 and the separate band body member 21A.

A male member (or a female member) 31 of the hook and loop fastener 3 generally referred to as a magic tape (registered trademark) is provided on the inner surface side of a portion near a left end of the band body 2 illustrated in FIG. 1 (i.e., one end portion of the band body 2 in the longitudinal direction of the band body 2). A female member (or a male member) 32 of the hook and loop fastener 3 is provided on the inner surface side of a portion near a right end of the band body 2 illustrated in FIG. 1 (i.e., the opposite end portion of the band body 2 in the longitudinal direction of the band body 2 from the one end portion). As illustrated in FIG. 2, for example, when the male member 31 and the female member 32 of the hook and loop fastener 3 are joined to each other, the band body 2 may be detachably installed with respect to the wrist H while being wound around the outer circumference of the wrist H.

The fixing means of the band body 2 is not restricted to the hook and loop fastener 3 illustrated in FIG. 1. For example, it is possible to employ a snap, a button, a clip, and/or a frame member that connects the end portions of the band body 2.

As illustrated in FIG. 2 and described above, the reinforcing plate 4 is held by the band body 2 by being inserted between the doubly formed (i.e., overlapping) reinforcing plate holder 21 of the band body 2. The curved reinforcing plate 4 has a shape in which at least a portion is curved toward an inner circumferential surface side (e.g., the end portions of the reinforcing plate 4 may be curved towards the wrist of the patient). The reinforcing plate 4 is made of a harder material than that of the band body 2 (i.e., the reinforcing plate 4 is more rigid than the band body 2), and maintains a nearly constant shape.

As illustrated in FIG. 1, the reinforcing plate 4 has a shape which is elongated in the longitudinal direction of the band body 2. As illustrated in FIG. 2, a central part 41 of the reinforcing plate 4 in a longitudinal direction is scarcely curved and has a flat plate shape. A curved portion 42 of the reinforcing plate 4 is curved toward an inner circumference side and along the longitudinal direction of the band body 2 (i.e., the circumferential direction of the wrist H). A curved portion 42 is formed at each of the two sides of the central part 41 of the reinforcing plate 4 as illustrated in FIG. 2. A radius of curvature R2 of the curved portion 42 is smaller than a radius of curvature R1 of the central part 41 (in an illustrated configuration, the radius of curvature R1 is nearly infinite).

The reinforcing plate 4 material is not particularly restricted and may be a material which allows the operator to visually recognize the puncture site 100 through the reinforcing plate 4. Examples of the constituent material of the reinforcing plate 4 include acrylic resin, polyvinyl chloride (particularly, rigid polyvinyl chloride), polyethylene, polypropylene, polyolefin such as polybutadiene, polystyrene, poly-(4-methylpentene-1), polycarbonate, ABS resin, polymethylmethacrylate (PMMA), polyacetal, polyacrylate, polyacrylonitrile, polyvinylidene fluoride, ionomer, an acrylonitrile-butadiene-styrene copolymer, polyethylene terephthalate (PET), polyester such as polybutylene terephthalate (PBT), a butadiene-styrene copolymer, aromatic or aliphatic polyamide, a fluorine-based resin such as polytetrafluoroethylene.

It is preferable that the reinforcing plate 4 be substantially transparent. This may allow the operator to reliably visually recognize the puncture site 100 from the outside through the band body 2 and the reinforcing plate 4. The operator may thus easily position the marker 7 (described below) at the puncture site 100. The reinforcing plate 4 may have a shape which does not include a non-curved portion such as the central part 41. In other words, in some embodiments the reinforcing plate 4 may be curved across the whole length of the reinforcing plate 4.

As illustrated in FIG. 1 and FIG. 2, the balloon 5 is connected to the inner surface side (i.e., a side touching the skin of the patient) of the band body 2. The balloon 5 is made of a material having flexibility. The balloon 5 is an example of an expansion member which can be dilated by injecting a fluid (e.g., air). In this way, air may be injected into the balloon 5 between the band body 2 and the wrist H to dilate the balloon 5 and to apply pressure to the puncture site 100 on the wrist 100.

As illustrated in FIG. 2, the balloon 5 is connected to the inner surface side of the band body 2 through an interlock portion 11 having flexibility. The balloon 5 is one-sided toward one end side of the reinforcing plate 4 in the longitudinal direction on the inner surface side of the band body 2. In other words, the balloon 5 is off-center with respect to the middle portion of the reinforcing plate 4 in the longitudinal direction of the band body 2. As illustrated in FIG. 2, the balloon 5 is positioned to overlap a portion on a nearly right half side of the reinforcing plate 4. For example, the balloon 5 is formed in a pouch shape (e.g., an ovular shape) by sealing an edge portion of a sheet material containing the above-described material through welding or adhesion. The balloon 5 has a rectangular shape when the balloon 5 is not dilated by injection of air.

As illustrated in FIG. 2, when the interlock portion 11 has a relatively short length, the balloon 5 is positioned at a location which is on one side with respect to the reinforcing plate 4 in the longitudinal direction of the reinforcing plate 4. It is preferable that the balloon 5 be formed using the same material as, or a similar material to, that of the band body 2. It is preferable that a material contained in the interlock portion 11 be the same as a material contained in the balloon 5. The balloon 5 may thus be easily joined to the inner surface side of the band body 2 through welding (or another connecting method as described above) using the interlock portion 11.

The material contained in the balloon 5 is not particularly restricted and may be a material which allows the operator to visually recognize the puncture site 100 from the outside through the band body 2, the reinforcing plate 4, and the balloon 5. It is preferable that the band body 2 and the balloon 5 be substantially transparent. The operator may thus reliably visually recognize the puncture site 100 from the outside through the band body 2, the reinforcing plate 4, and the balloon 5. Further, the marker 7 may be more easily positioned by the operator with respect to the puncture site 100 when the operator views the marker 7 from the outside through the band body 2 and the balloon 5.

As illustrated in FIG. 1 and FIG. 2, the marker 7 is provided on an inner surface side of the balloon 5. That is, the marker 7 is provided on a surface side touching the puncture site 100. When the marker 7 is provided on the inner surface side of the balloon 5, the operator may more easily position the balloon 5 with respect to the puncture site 100 on the wrist H of the patient using the marker 7 while visually recognizing the puncture site 100 through the band body 2, the reinforcing plate 4, and the balloon 5. This configuration makes it is possible to prevent leakage of blood from the puncture site 100 or generation of a hematoma due to a position aberration of the balloon 5.

As illustrated in FIG. 1, the center of the marker 7 is preferably provided at the central portion of the balloon 5. In other words, the marker 7 is preferably provided at an intersection point of diagonal lines of a rectangle corresponding to the balloon 5 such that it is at the central portion of the balloon 5. In this way, the central portion of the balloon 5 may be positioned with respect to the puncture site 100 by the operator, and thus a pressure force of the balloon 5 may reliably act on the puncture site 100 when the balloon 5 is dilated. A shape of the marker 7 is not particularly restricted. Examples of the shape of the marker 7 include a circle, a triangle, and a rectangle. In FIG. 1, the marker 7 has a rectangular shape.

The material of the marker 7 is not particularly restricted. Examples of the material of the marker 7 include oil coloring matter such as ink and a resin obtained by kneading and mixing a pigment. The method of providing the marker 7 in the balloon 5 is not particularly restricted. Examples of the application method include printing the marker 7 on the balloon 5, welding the marker 7 to the balloon 5, and applying an adhesive to one surface of the marker 7 to attach the marker 7 to the balloon 5.

The color of the marker 7 is not particularly restricted as long as the color allows the balloon 5 to be positioned to the puncture site 100. Green is a preferable color. When green is used, the operator may easily visually recognize the marker 7 on blood or the skin through the band body 2, the reinforcing plate 4, and the balloon 5, and thus the balloon 5 may be more easily positioned at the puncture site 100.

In addition, it is preferable that the marker 7 be translucent. In this way, the operator may visually recognize the puncture site 100 from the outside of the marker 7. The marker 7 may be provided on an inner surface side of the balloon 5 (i.e., inside the balloon). In other words the marker 7 may be provided on the opposite surface from the surface of the balloon 5 that touches the puncture site 100 (i.e., the reverse side of the side illustrated in FIG. 1). In addition, the marker 7 may be provided on the band body 2, the reinforcing plate 4, or the auxiliary balloon 6 (described below) rather than on the balloon 5. In any of these alternative embodiments, the marker 7 is provided to overlap the central portion of the balloon 5.

As illustrated in FIG. 1 and FIG. 2, the auxiliary balloon 6 is disposed between the balloon 5 and the curved portion 42 of the reinforcing plate 4 of the band body 2. The auxiliary balloon 6 is made of a material having flexibility and is disposed to overlap the balloon 5. When air is injected into the auxiliary balloon 6 and the balloon 5, the auxiliary balloon 6 functions as an expansion member which presses against the balloon 5 to apply a pressure force on an outer surface of the balloon 5.

The material within the auxiliary balloon 6 may be a material that allows the operator to visually recognize the puncture site 100. The same material as the material contained in the balloon 5 may be employed. It is preferable that the auxiliary balloon 6 be substantially transparent. The operator may thus visually recognize the puncture site 100 on the wrist H of the patient through the band body 2, the reinforcing plate 4, the auxiliary balloon 6, and the balloon 5 to more easily position the marker 7 at the puncture site 100.

As illustrated in FIG. 2, when the auxiliary balloon 6 is formed such that a width of the auxiliary balloon 6 in the longitudinal direction of the band body 2 is smaller than the balloon 5, the auxiliary balloon 6 is disposed between the balloon 5 and the curved portion 42 of the reinforcing plate 4. Thus, the auxiliary balloon 6 locally presses the balloon 5 (i.e., directly contacts the outer surface of the balloon 5 to apply a pressing force). In this way, a direction of a pressing force F from the balloon 5 to the puncture site 100 may be more reliably inclined (i.e., the pressing force F may be more reliably controlled so that the pressing force aligned with or directed at the puncture site 100).

In addition, the auxiliary balloon 6 touches/contacts the curved portion 42 of the curved plate 4 or a portion on a right side of the curved portion 42 of FIG. 2. In this way, a direction of the force received by the auxiliary balloon 6 from the curved plate 4 (i.e., a normal direction of the reinforcing plate 4 at a portion touched by the auxiliary balloon 6 through the band body 2) is inclined in a direction toward a central portion G of the wrist H. As a result, the direction of the pressing force F or a pressing force f may be more reliably inclined (i.e., the pressing force F may be more reliably controlled to be aligned with the puncture site 100).

As illustrated in FIG. 2, a portion of the balloon 5 and a portion of the auxiliary balloon 6 are joined to each other using a method such as welding or adhesion. In addition, a communicating section (opening portion) 12 that allows communication between an inside of the balloon 5 and an inside of the auxiliary balloon 6 is formed in a joint portion. In this way, when liquid (e.g., air) is injected into the balloon 5 as described above, a portion of injected liquid flows into the auxiliary balloon 6 through the communicating section 12. The auxiliary balloon 6 thus dilates in association with the dilation of the balloon 5. Therefore, the balloon 5 and the auxiliary balloon 6 may be dilated by performing an air injection operation once and operability of air injection is excellent (i.e., an operator may effectuate a more efficient/easier air injection operation).

As illustrated in FIG. 2, the auxiliary balloon 6 is connected to the inner surface side of the band body 2 on the same side as the interlock portion 11 of the balloon 5 (a right position of FIG. 2) through a bonded portion 13. In this way, the auxiliary balloon 6 is more easily and reliably inclined. Thus, the pressing force f with respect to the balloon 5 more easily acts in an inclined direction (direction in which the balloon 5 nearly faces the central portion G of the wrist H), and an improved hemostatic effect may be obtained.

The pressing member that presses the balloon 5 towards the central portion G of the wrist H is not restricted to an auxiliary balloon 6. For example, it is possible to employ a member such as a pad containing a sponge-like material, an elastic material, a fiber assembly such as cotton, or a combination of these components.

Next, a description will be given of an air (i.e., a type of fluid) injection portion 50 illustrated in FIG. 1.

The injection portion 50 includes a tube 51 and a bag body 52. The bag body 52 is an example of an airtight space having a constant volume, and the bag body 52 functions as a buffer. In addition, the injection portion 50 forms an injection passage that connects a connector 60 to the balloon 5 or the auxiliary balloon 6. The tube 51 is a flexible tube. One end portion 51A of the tube 51 is connected to a connection section 5R of the balloon 5. The other end portion 51B of the tube 51 is connected to a connection section 52A of the bag body 52. The bag body 52 has the connection section 52A in one end portion and has the connector 60 in the other end portion.

Next, a description will be given of a constructional example of the syringe 200 corresponding to a fluid supply member in reference to FIG. 1.

The syringe 200 illustrated in FIG. 1 is normally used as the fluid supply member to supply air into the balloon 5 and the auxiliary balloon 6. The syringe 200 includes a cylindrical main container portion 201, a protruding portion 202, and a plunger 203. The protruding portion 202 is provided at one end portion of the main container portion 201. The plunger 203 is inserted into the other end portion of the main container portion 201. The protruding portion 202 may be connected to the bag body 52 by being inserted into the connector 60.

As described above, when the protruding portion 202 is inserted into the connector 60, a valve body (not illustrated) is pressed. This allows a fluid passage inside the connector 60 to be opened.

When the operator presses the plunger 203, air (i.e., a type of fluid) inside the main container portion 201 may be injected into the balloon 5 and the auxiliary balloon 6 through a fluid passage of the protruding portion 202 and the fluid passage of the connector 60 and through the bag body 52 and the tube 51.

Next, a description will be given of a constructional example of the pressure adjustment unit 110 illustrated in FIG. 1 with reference to FIG. 3 and FIG. 4.

Figure 3:
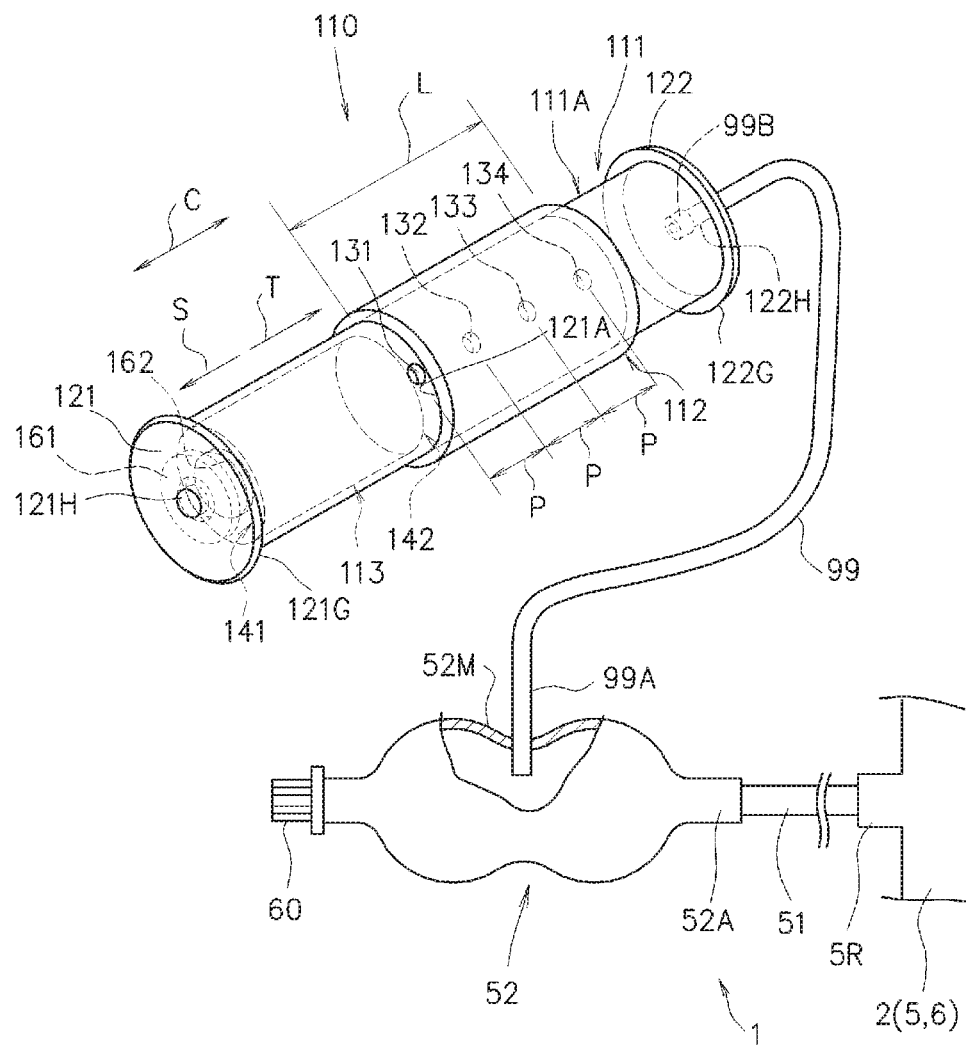
FIG. 3 is a perspective view illustrating shape examples of a bag body and a pressure adjustment unit of the hemostatic instrument shown in FIG. 1.

FIG. 3 is a perspective view illustrating examples of the bag body 52 and the pressure adjustment unit 110 of the embodiment illustrated in FIG. 1. FIG. 4 is a front view having a partial cross section illustrating a constructional example of the pressure adjustment unit 110 illustrated in FIG. 3. The pressure adjustment unit 110 may be referred to as a pressure force pressure adjustment unit. The pressure adjustment unit 110 adjusts pressure by extracting a part of the fluid (e.g., air) inside the balloon 5 and the auxiliary balloon 6 to reduce the pressure force of the balloon 5 and the auxiliary balloon 6.

When bleeding is stopped at the puncture site 100 illustrated in FIG. 2 using the balloon 5 of the above-described air injection type pressing hemostatic instrument 1, a hole of a blood vessel is blocked by a blood clot, and the like over time. Thus, when pressing is performed at an initially set pressure force without change using the hemostatic instrument, the blood flow in a blood vessel may be hindered, or numbness or pain may be caused to the patient.

For this reason, the operator stops the bleeding at the puncture site 100 over several hours while periodically reducing the pressure force caused by the hemostatic instrument. In other words, the operator performs an operation of reducing the pressure of the balloon. The pressure adjustment unit 110 illustrated in FIG. 1, FIG. 3, and FIG. 4 is used to reduce the pressure force applied by the balloon 5 to the puncture site 100 through a simple operation of the operator.

As illustrated in FIG. 3, the pressure adjustment unit 110 is connected to the bag body 52 by a tube 99. One end portion 99A of the tube 99 is connected to a middle part 52M of the bag body 52, and the other end portion 99B of the tube 99 is connected to an end portion (communication port) of the pressure adjustment unit 110 in advance. The tube 99 is made of a flexible material similar to the tube 51 illustrated in FIG. 1. The pressure adjustment unit 110 may be connected to a portion at which fluid is injected from the injection portion 50. For example, the tube 99 may be connected to the balloon 5, the auxiliary balloon 6, and the tube 51.

Figure 4:
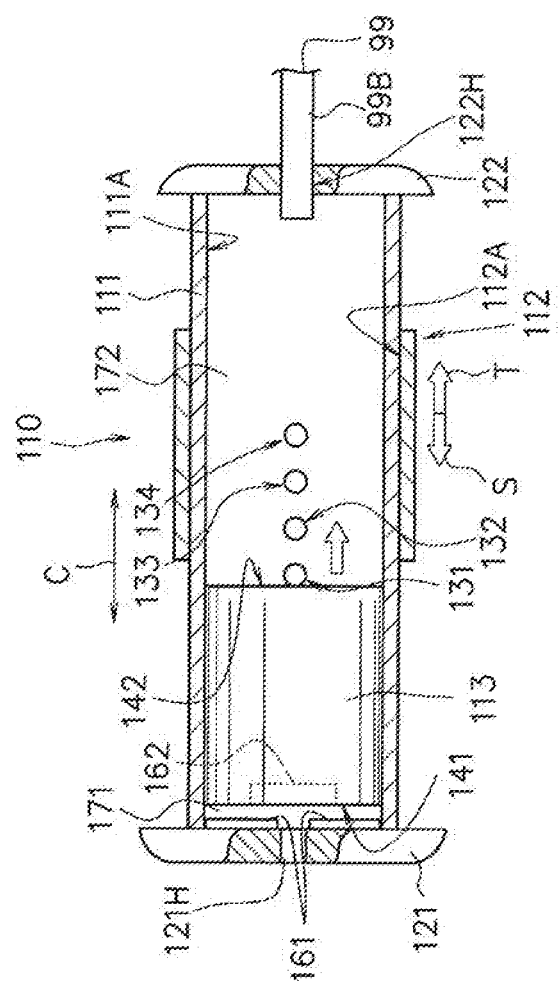
FIG. 4 is a partial cross section of a front view illustrating a constructional example of the pressure adjustment unit illustrated in FIG. 3.
Figure 5:
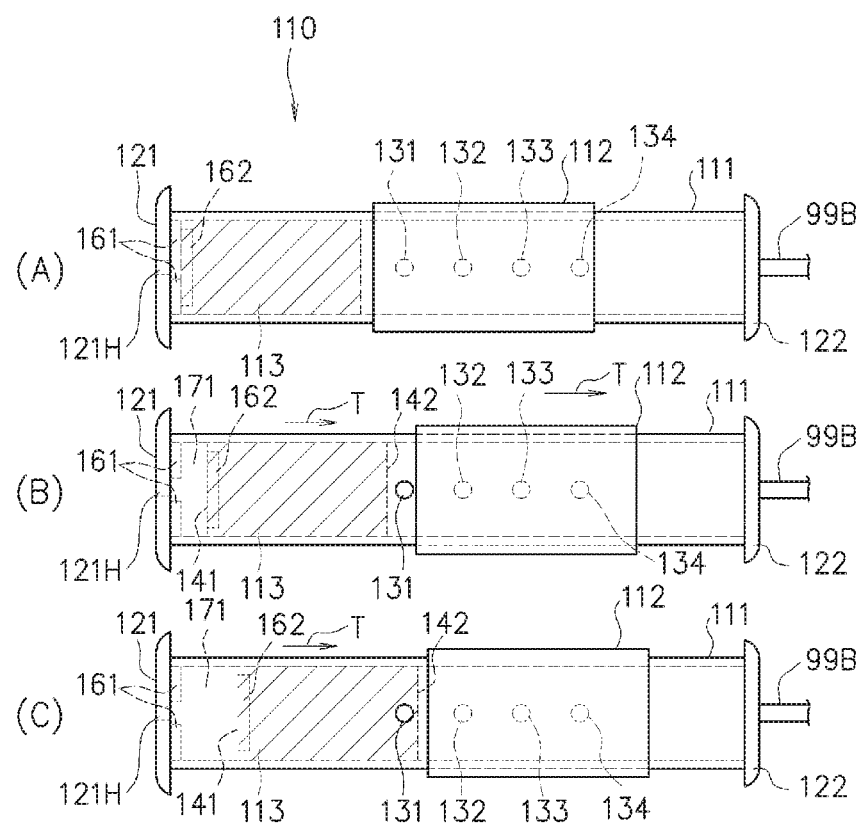
FIG. 5 is a diagram illustrating a sequence in which an operator adjusts the pressure force caused by the hemostatic instrument in a plurality of stages for each arbitrary elapsed time by manually operating the pressure adjustment unit.
Figure 6:
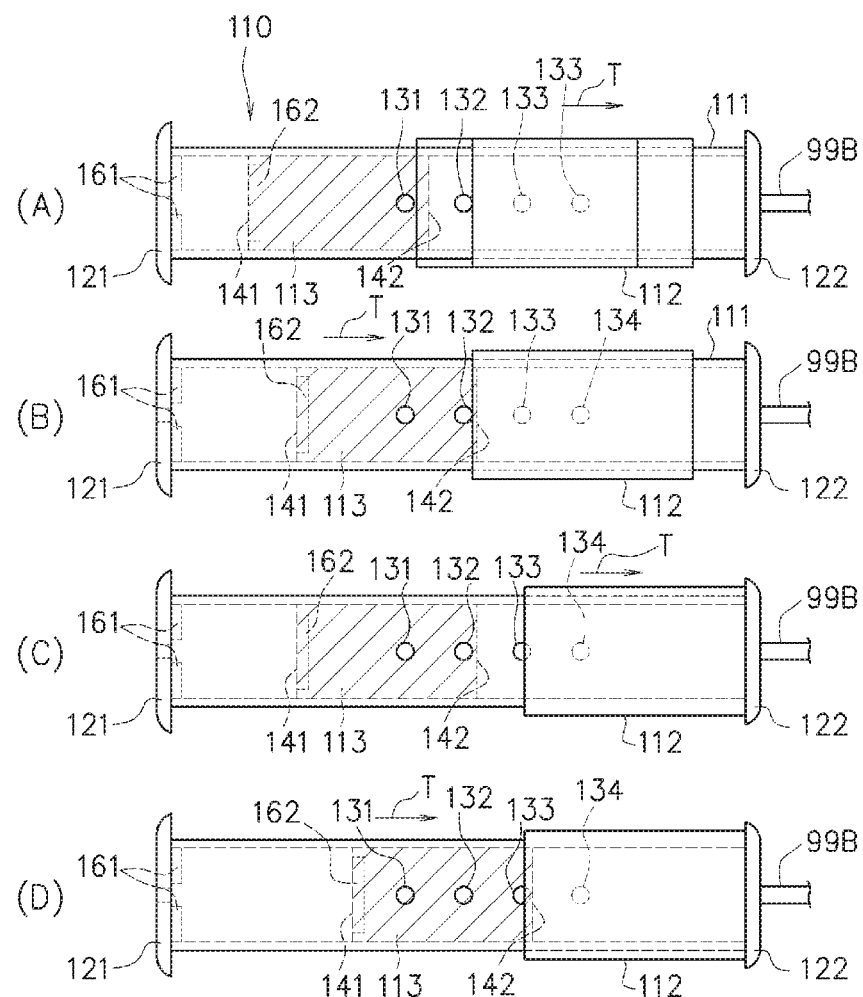
FIG. 6 is a diagram illustrating a sequence of performing adjustment of the pressure force subsequent to the adjustment of the pressure force illustrated in FIG. 5.

As illustrated in FIG. 3 and FIG. 4, the pressure adjustment unit 110 includes a main container portion 111, a sliding member 112, a moving body 113 such as a gasket, and a force applying means (e.g., a first magnet 161 and a second magnet 162 in the embodiment illustrated in FIGS. 3 and 4). The first magnet 161 and the second magnet 162 are made from a hard magnetic material or a soft magnetic material. A permanent magnet using the hard magnetic material is preferably used to obtain durability of performance or sufficient magnetic intensity suitable for an object.

However, the first and second magnets 161, 162 are not restricted to a "permanent magnet", and may use an "electromagnet".

It is preferable that the main container portion 111 illustrated in FIG. 3 and FIG. 4 be made of glass or plastic which is transparent or translucent. The main container portion 111 is a cylindrical member. A circular cover member 121 is provided at one end portion of the main container portion 111, and a circular cover member 122 is provided at the other end portion of the main container portion 111. The internal space of the main container portion 111 is closed by the cover member 121 in the one end portion and the cover member 122 in the other end portion, and thus the interior of the main container portion 111 is closed from ambient air.

It is preferable that a through-hole 121H be formed at a central position of the cover member 121 (i.e., at a center point of the circular cover member 121).

A first space formed between the cover member 121 and the moving body 113 formed inside the main container portion 111 may be maintained in a state of atmospheric pressure. Specifically, when the operator moves the sliding member 112 to open a first air passing hole 131, the moving body 113 moves in a direction of the cover member 122 inside the main container portion 111 when there is a pressure reduction of the expansion member (the balloon 5 and the auxiliary balloon 6). The first space formed between the cover member 121 and the moving body 113 formed inside the main container portion 111 has the through-hole 121H, and thus is not in a vacuum state. Therefore, the moving body 113 may be easily moved inside the main container portion 111. In other words, the through-hole 121H prevents a vacuum from occurring.

In an initial state illustrated in FIG. 3 and FIG. 4, for example, the main container portion 111 has four passing holes 131, 132, 133, 134—the first air passing hole 131 to a fourth air passing hole 134 as air passing holes. The four air passing holes 131, 132, 133, 134 may be formed at equal intervals P with respect to the adjacent passing hole in parallel with an axial direction C of the main container portion 111 on the outer circumferential surface of the main container portion 111. In other words, the axial spacing between axially adjacent holes may be the same. The respective intervals P of the air passing holes 131 to 134 are determined based on a magnetic force acting between the first magnet and the second magnet. When the plurality of air passing holes are on the outer circumferential surface of the main container portion 111, it is preferable that the intervals P between adjacent air passing holes increase from the cover member 121 toward the cover member 122. That is, the magnetic force acting between the first magnet and the second magnet weakens as the distance between the first magnet and the second magnet increases. For this reason, it is preferable that the intervals P increase from the cover member 121 toward the cover member 122 in order to maintain a constant pressure reduction degree of the expansion member when the respective air passing holes are opened. For example, the first air passing hole 131 to the fourth air passing hole 134 have circular shapes and are through-holes formed through the outer circumferential surface of the main container portion 111. In this example, the first air passing hole 131 to the fourth air passing hole 134 are formed side by side in series in a nearly middle position of the main container portion 111.

The moving body 113 such as a gasket is accommodated inside the main container portion 111. The moving body 113 is movable in a direction T and a direction S. The moving body 113 is a cylindrical member made of rubber or plastic. The outer circumferential surface of the moving body 113 and the inner circumferential surface of the main container portion 111 are airtight such that there is no leakage of air between these surfaces. In the initial state illustrated in FIG. 3 and FIG. 4, one end portion 141 of the moving body 113 is positioned around/near an inner surface of the cover member 121 or contacts the inner surface of the cover member 121. In the embodiment illustrated in FIG. 3 and FIG. 4, the second magnet is disposed in the one end portion 141 of the moving body 113. In addition, the one end portion 141 of the moving body 113 is positioned around/near the inner surface of the cover member 121 in the initial state. The other end portion 142 of the moving body 113 is positioned on the cover member 121 side from the first air passing hole 131 (i.e., the other end portion 142 of the moving body 113 is closer to the cover member 121 than the first air passing hole 131 when the moving body 113 is in the initial state). For this reason, the moving body 113 does not block the first air passing hole 131 to the fourth air passing hole 134 (i.e., any of the plurality of air passing holes 131-134). Note that the initial state is when a pressure reducing operation is not performed while the expansion member (the balloon 5 and the auxiliary balloon 6) is dilated to press a region (e.g., a puncture site) in which bleeding needs to be stopped. The state in which the pressure reducing operation is not performed refers to a state in which the respective air passing holes of the main container portion 111 are not opened by moving the sliding member 112 (i.e., the sliding member 112 blocks all of the air passing holes 131-134). As an additional point, it is noted that before the expansion member of the hemostatic instrument is dilated, the other end portion 142 of the moving body 113 touches/contacts an inner surface of the cover member 122 due to the repulsive force acting between the first magnet and the second magnet.

The sliding member 112 illustrated in FIG. 3 and FIG. 4 is a cylindrical member, and an inner circumferential surface 112A of the sliding member 112 touches an outer circumferential surface 111A of the main container portion 111 in an airtight state such that air does not leak between these surfaces. The sliding member 112 has a length in an axial direction C such that all of the air passing holes 131-134 (i.e., the first air passing hole 131 to the fourth air passing hole 134) can be covered. When the operator slides the sliding member 112 in the direction T along the main container portion 111, the first air passing hole 131 to the fourth air passing hole 134 blocked by the sliding member 112 are opened one by one in sequential order.

Similar to the main container portion 111, it is preferable that the sliding member 112 be made of glass or plastic which is transparent or translucent. When the sliding member 112 is transparent or translucent, the operator may easily visually recognize positions of the first air passing hole 131 to the fourth air passing hole 134 of the main container portion 111 through the sliding member 112. The operator may also easily visually recognize a position of the moving body 113 through the sliding member 112 and the main container portion 111.

When the operator holds the sliding member 112 with the operator's fingers, the sliding member 112 is slidable in the direction T and the direction S parallel to the axial direction C along the outer circumferential surface 111A of the main container portion 111. The direction T is a direction toward the cover member 122 on the other side, and the direction S is a direction toward the cover member 121 on one side (i.e., the side opposite to the other side).

A length L of the sliding member 112 along the axial direction C is preferably set so that at least the first air passing hole 131 to the fourth air passing hole 134 can be simultaneously covered.

The cover member 121 and the cover member 122 of the main container portion 111 function as a retaining inhibition member when the sliding member 112 is slid. That is, the outer diameter dimensions of the cover member 121 and the cover member 122 are larger than external dimensions of the outer circumferential surface 111A of the main container portion 111. The cover member 121 has a retaining inhibition portion 121G, and the cover member 122 has a retaining inhibition portion 122G.

The retaining inhibition portions 121G, 122G are disposed so that when the operator slides the sliding member 112 in the direction S, the sliding member 112 collides with the retaining inhibition portion 121G of the cover member 121. The operator thus will not remove the sliding member 112 from the main container portion 111. When the operator slides the sliding member 112 in the direction T, the sliding member 112 collides with the retaining inhibition portion 122G of the cover member 122 on the opposite side. Thus, the operator does not erroneously remove the sliding member 112 from the main container portion 111.

In addition, as illustrated in FIG. 3 and FIG. 4, the pressure adjustment unit 110 includes a first magnet 161 and a second magnet 162. The second magnet 162 is fixed to the one end portion 141 of the moving body 113. The second magnet 162 may instead be fixed to the other end portion 142 of the moving body 113. The first magnet 161 is fixed to the inner surface of the cover member 121. In the illustrated embodiment, the first magnet 161 and the second magnet 162 are permanent magnets. For example, S-pole sides of the first magnet 161 and the second magnet 162 face each other. Alternatively, N-pole sides of the first magnet 161 and the second magnet 162 face each other. This configuration leads to a repulsive force which acts between the first magnet 161 and the second magnet 162 (i.e., to urge the second magnet 162 toward the cover member 122 on the opposite side).

The first space is formed between the moving body 113 and the cover member 121 inside the main container portion 111, and a second space is formed between the moving body 113 and the cover member 122. When the expansion member is depressurized, the moving body 113 moves toward the cover member 122 inside the main container portion 111 to form the first space and the second space inside the main container portion 111. Herein, the first space is a space formed between the one end portion 141 of the moving body 113 and the cover member 121, and is formed based on the repulsive force acting between the first magnet and the second magnet. The second space is a space formed between the other end portion 142 of the moving body 113 and the cover member 122, and is formed based on the internal pressure of the expansion body. When fluid inside the expansion member is discharged through the air passing holes, the moving body 113 moves to the cover member 122 by the repulsive force acting between the first magnet and the second magnet to block the opened air passing holes. In this instance, when the moving body 113 moves and blocks the opened air passing holes, the pressure adjustment unit 110 may maintain a pressure inside the expansion member while reducing the pressure inside the expansion member.

Next, a description will be given of an example of use of the above-described hemostatic instrument 1.

The band body 2 of the hemostatic instrument 1 illustrated in FIG. 1 is installed, for example, on the wrist H of the patient as illustrated in FIG. 2. Before installation, however, air is not injected into the balloon 5 and the auxiliary balloon 6, and so the balloon 5 and the auxiliary balloon 6 are not dilated (i.e., remain deflated).

When the band body 2 illustrated in FIG. 1 is installed on the wrist H as illustrated in FIG. 2, the puncture site 100 to an artery is normally located at a position off-center to the thumb side on the inside (a side at which a tendon is present) of the wrist H (i.e., the puncture site is closer to the edge of the thumb-side of the wrist than to the pinky-side of the wrist). An introducer sheath is indwelled in the puncture site 100. The band body 2 is wound around the wrist H in a state in which the introducer sheath is indwelled, and the balloon 5 is positioned such that the marker 7 provided in the balloon 5 is superposed on (i.e., placed directly over) the puncture site 100. The end portions of the band body 2 are fixed by the hook and loop fastener 3.

After the hemostatic instrument 1 illustrated in FIG. 1 is installed on the wrist H, the operator inserts and fits the protruding portion 202 of the syringe 200 into the connector 60 of the injection portion 50 illustrated in FIG. 3. When the protruding portion 202 of the syringe 200 is pushed into an inner circumferential surface portion of the connector 60, the protruding portion 202 of the syringe 200 pushes the valve body inside the connector 60 to open the valve body.

When the operator presses the plunger 203 of the syringe 200, air (i.e., a type of fluid) inside the main container portion 201 is injected into the balloon 5 and the auxiliary balloon 6 through a passage of air (fluid) inside the connector 60, the bag body 52, and the tube 51. The balloon 5 and the auxiliary balloon 6 may thus be dilated (i.e., inflated) at a predetermined air pressure. When air is injected, a dilation level of the balloon 5 and the auxiliary balloon 6, that is, a pressure force to the puncture site 100, may be adjusted according to the needs of the patient using the injected amount of air.

After the balloon 5 and the auxiliary balloon 6 are dilated as described above, the protruding portion 202 of the syringe 200 is removed from the connector 60. The valve body inside the connector 60 prevents air from leaking because the inside of the inner circumferential surface portion is closed. That is, when the protruding portion 202 of the syringe 200 is removed, the valve body illustrated in FIG. 3 is closed. Thus, air inside the balloon 5 and inside the auxiliary balloon 6 does not leak out of the connector 60. The introducer sheath is then removed from the puncture site 100.

As illustrated in FIG. 2, the balloon 5 and the auxiliary balloon 6 may maintain in a dilated state and may maintain a state of pressing the puncture site 100. In this dilated state, the balloon 5 locally presses the puncture site 100 and a portion around the puncture site 100. The reinforcing plate 4 is separated from a surface of the wrist H and rarely touches the wrist H due to dilation of the balloon 5 and the auxiliary balloon 6. The pressure force is thus concentrated on the puncture site 100 and the portion around the puncture site 100, and thus hemostatic effect is high. Additionally, another blood vessel or nerve that is not bleeding may be prevented from being pressed. For this reason, numbness of a hand, poor circulation, and the like are prevented.

When the band body 2 of the above-described air injection type pressing hemostatic instrument 1 illustrated in FIG. 1 is used, a hole of a blood vessel is blocked by a blood clot and the like over time. The blood flow of the blood vessel may thus be hindered, or numbness or pain may be generated. In order to avoid such inconvenience to the patient, the operator performs an operation of stopping bleeding over several hours while manually performing an operation of reducing the pressure force exerted by the hemostatic instrument 1 in a plurality of stages for an arbitrary elapsed time. In other words, the operator performs an operation of periodically reducing the air pressure of the balloon 5 and the auxiliary balloon 6. The operator may stop bleeding over several hours by reducing a pressure force caused by the hemostatic instrument 1 in a plurality of stages for an arbitrary elapsed time using the pressure adjustment unit 110 illustrated in FIG. 1, FIG. 3, and FIG. 4.

FIGS. 5(a) to 6(D) illustrate a sequence in which the operator adjusts a pressure force caused by the hemostatic instrument 1 in a plurality of stages for each arbitrary elapsed time by manually operating the pressure adjustment unit 110.

First, FIG. 5(A) illustrates an initial state at the time of operating the pressure adjustment unit 110. In FIG. 5(A), the balloon 5 and the auxiliary balloon 6 are in a dilated state (e.g., as illustrated in FIG. 2). The pressure adjustment unit 110 starts adjusting pressure when bleeding at the puncture site 100 stops by pressing the puncture site 100. In the initial state at the time of operating the pressure adjustment unit 110, the balloon 5 and the auxiliary balloon 6 are in the dilated state, and the sliding member 112 blocks the air passing holes 131-134 from the first air passing hole 131 to the fourth air passing hole 134 of the main container portion 111. The other end portion 142 of the moving body 113 is positioned on the cover member 121 side relative to the first air passing hole 131 (i.e., the other end portion 142 of the moving body 113 is closer to the cover member 121 than the first air passing hole 131 when the moving body 113 is in the initial state).

When stopping of bleeding starts as illustrated in FIG. 5(A), the moving body 113 is positioned near the inner surface of the cover member 121 inside the main container portion 111 (or in contact with the inner surface of the cover member 121). For example, as shown in FIG. 5(a), the moving body 113 is positioned so as to be axially spaced from all of the through holes 131-134 so that the moving 113 body does not axially overlap any of the through holes 131-134. The first air passing hole 131 to the fourth air passing hole 134 are blocked by the sliding member. For this reason, while air inside the balloon 5 and the auxiliary balloon 6 communicates with an inside of the main container portion 111 of the pressure adjustment unit 110 through the tube 51, the bag body 52, and the tube 99 illustrated in FIG. 1, the air inside the balloon 5 and the auxiliary balloon 6 does not leak from any one of the first air passing hole 131 to the fourth air passing hole 134. The moving body 113 moves to the cover member 121 side against a repulsive force acting between the first magnet 161 and the second magnet 162 because of the pressure applied by the air inside the balloon 5 and the auxiliary balloon 6. Therefore, in the initial state of FIG. 5(A), the volume of the second space formed between the other end portion 142 of the moving body 113 and the cover member 122 is maximized.

Next, FIG. 5(B) illustrates a state in which the operator attempts to reduce a pressure force (pressure) caused by the balloon 5 and the auxiliary balloon 6 using the pressure adjustment unit 110. After a certain time (for example, one hour) from when stopping of bleeding starts, the operator slightly slides the sliding member 112 in the direction T such that the first air passing hole 131 is opened from the sliding member 112. The moving body 113 then moves to the cover member 122 side due to the repulsive force acting between the first magnet 161 and the second magnet 162 to block the first air passing hole 131. In this instance, a repulsive force (internal pressure) of the first space formed between the one end portion 141 of the moving body 113 and the cover member 121 is identical to an internal pressure of the second space formed between the other end portion 142 of the moving body 113 and the cover member 122. In addition, the pressure force caused by the balloon 5 and the auxiliary balloon 6 is reduced equal to the reduced air inside the balloon 5 and the auxiliary balloon 6.

When the first air passing hole 131 is opened by moving the sliding member 112 as illustrated in FIG. 5(B), and air inside the balloon 5 and the auxiliary balloon 6 leaks out of the main container portion 111 through the first air passing hole 131. It is thus possible to reduce the pressure (pressure force) of the balloon 5 and the auxiliary balloon 6.

Since the pressure of the balloon 5 and the auxiliary balloon 6 decreases, the moving body 113 moves in the direction T to close the first air passing hole 131 as illustrated in the sequence shown in FIGS. 5(B) to 5(C). The second air passing hole 132, the third air passing hole 133, and the fourth air passing hole 134 remain covered/closed by the sliding member 112. For this reason, air inside the balloon 5 and the auxiliary balloon 6 does not leak out of the main container portion 111 from the inside of the main container portion 111. In addition, since the moving body 113 blocks the first air passing hole 131, the repulsive force acting between the first magnet 161 and the second magnet 162 becomes equal to an internal pressure (pressure) of the expansion member. The moving body 113 thus remains positioned at this location. The first space formed between the one end portion 141 of the moving body 113 and the inner surface of the cover member 121 may not be sealed. For this reason, the moving body 113 may have a size at which one air passing hole can be closed.

Next, FIG. 6(A) illustrates a state in which the operator attempts to further reduce the pressure force (pressure) exerted by the balloon 5 and the auxiliary balloon 6 on the puncture site 100 using the pressure adjustment unit 110. The sliding member 112 is first positioned over the second air passing hole 132 (the left box illustrated in FIG. 6(A)). When another certain time (for example, one hour) passes, the operator again slightly slides the sliding member 112 in the direction T as illustrated in FIG. 6(A) from a pressure reduction state illustrated in FIG. 5(B) and FIG. 5(C). The sliding member 112 is moved in this way to no longer cover the second air passing hole 132 (the right box illustrated in FIG. 6(A)).

Since the second air passing hole 132 is opened from movement of the sliding member 112 illustrated in FIG. 6(A), air inside the balloon 5 and the auxiliary balloon 6 leaks out of the main container portion 111 through the second air passing hole 132. The pressure (pressure force) of the balloon 5 and the auxiliary balloon 6 may thereby be further reduced. When the pressure of the balloon 5 and the auxiliary balloon 6 further decreases, the moving body 113 slightly moves in the direction T to close from the first air passing hole 131 to the second air passing hole 132 as illustrated in the sequence shown in FIG. 6(A) to FIG. 6(B). The moving body 113 may be configured to block only the second air passing hole 132 depending on the size of the moving body 113. In addition, the sliding member 112 closes the third air passing hole 133 and the fourth air passing hole 134. Air inside the balloon 5 and the auxiliary balloon 6 thus does not leak out of the main container portion 111 from the inside of the main container portion 111 after the moving body 113 moves to block the second air passing hole 132. Since the moving body 113 blocks the second air passing hole 132, the repulsive force acting between the first magnet 161 and the second magnet 162 becomes equal to the internal pressure (pressure) of the expansion member, and the moving body 113 remains positioned at this location.

FIG. 6(C) illustrates a state in which the operator further reduces the pressure force (pressure) exerted by the balloon 5 and the auxiliary balloon 6 on the puncture site 100 using the pressure adjustment unit 110 when stopping of bleeding ends. When another certain time (for example, one hour) passes, the operator slightly slides the sliding member 112 in the direction T from a pressure reduction state illustrated in FIG. 6(A) and FIG. 6(B).

In this way, since the third air passing hole 133 is opened from the sliding member 112 as illustrated in FIG. 6(C), air inside the balloon 5 and the auxiliary balloon 6 leaks out of the main container portion 111 through the third air passing hole 133. The pressure (pressure force) within the balloon 5 and the auxiliary balloon 6 may thus be further reduced. Since the pressure of the balloon 5 and the auxiliary balloon 6 is further reduced, the moving body 113 slightly moves in the direction T to close from the first air passing hole 131 to the third air passing hole 133 as illustrated from FIG. 6(C) to FIG. 6(D). For this reason, air inside the balloon 5 and the auxiliary balloon 6 does not leak out of the main container portion 111 from the inside of the main container portion 111.

As described above, the first air passing hole 131, the second air passing hole 132, and the third air passing hole 133 are opened one by one by gradually sliding the sliding member 112 in the direction T along the main container portion 111. After air is expelled from the main container portion 111, the moving body 113 blocks the first air passing hole 131, the second air passing hole 132, and the third air passing hole 133 one by one (i.e., in the same sequential manner as the operator's opening operations). Similarly, when the fourth air passing hole 134 is opened, the operator may further reduce the pressure in the balloon 5 and the auxiliary balloon 6. When the fourth air passing hole 134 of the main container portion 111 is opened, an internal pressure formed by air inside the balloon 5 and the auxiliary balloon 6 becomes smallest (i.e., relative to when the first through third air passing holes 131-133 are opened). The volume of the second space formed between the other end portion 142 of the moving body 113 and the cover member 122 is relatively thus the smallest. On the other hand, the volume of the first space formed between the one end portion 141 of the moving body 113 and the cover member 121 is relatively the greatest.

The operator may reduce the pressure force (pressure) caused by the balloon 5 and the auxiliary balloon 6 using the pressure adjustment unit 110 in a plurality of stages each time an arbitrary time passes from the time when stopping of the bleeding starts until stopping of the bleeding ends. Therefore, the operator may more easily arbitrarily adjust the pressure force in response to a state of the patient, and an effort of the operator to perform an operation of stopping bleeding may be reduced.

As illustrated in FIG. 3 and FIG. 4, the first magnet 161 and the second magnet 162 in the pressure adjustment unit 110 generate a repulsive force when the moving body 113 approaches the cover member 122 side. When a certain amount of the fluid (e.g., air) is discharged through an air passing hole from the inside of the main container portion 111 of the pressure adjustment unit 110, the moving body 113 may move by the repulsive force acting between the first magnet 161 and the second magnet 162 to block the opened air passing hole.

In the first embodiment described above, the one end portion 141 of the moving body 113 is positioned around (i.e., near to) the inner surface of the cover member 121 in the initial state illustrated in FIG. 5(A). However, the one end portion 141 may touch/contact the inner surface of the cover member 121.

In addition, four holes in total corresponding to the first air passing hole 131 to the fourth air passing hole 134 are illustrated in the main container portion 111 of the first embodiment to extract (i.e., release) a portion of air corresponding to fluid inside the balloon 5 and the auxiliary balloon 6 from the inside of the main container portion 111 to the outside. However, the invention is not limited to four holes. Two or three air passing holes or five or more air passing holes may be provided in the main container portion 111. Air may be released from the main container portion 111 in each of the embodiments in a plurality of stages, thereby reducing the pressure force (i.e., the internal pressure of the balloon 5 and auxiliary balloon 6).

In the first embodiment of the invention described above, the first magnet and the second magnet are used as the force applying means to apply a force that directs the moving body to a side at which the communication port is provided. However, the invention is not limited to using magnets. For example, a spring member may be used as the force applying means.

When the spring member is used as the force applying means, for example, the spring member is disposed between the cover member 121 and the one end portion 141 of the moving body in the pressure adjustment unit 110. The pressure adjustment unit 110 with the spring member does not include the first magnet 161 and the second magnet 162. The spring member may apply a force that directs the moving body 113 to a side at which the communication port is provided, and may or may not be connected to the cover member 121 or the moving body 113.

The spring member is a member that has an elastic force (i.e., the spring member is elastic). The spring member returns to a shape (natural state) formed before a force is applied when the force is applied. The spring member may represent a magnitude of a force applied to the spring member using a magnitude of expansion and contraction of the spring member. For example, the spring member may be a coil spring or a flat spring.

When the spring member is used as the force applying means, and when the expansion member is pressed, the moving body moves to an opposite side from a side at which the communication port inside the main container is provided. This movement is due to a pressure caused by fluid flowing in through the communication port of the main container portion from the expansion member. The spring member then deforms from a first shape formed before pressing (natural state) to a second shape deformed by pressing. When a fluid passing hole of the main container portion is opened to reduce a pressure of the expansion member, the spring member is subjected to a restoring force to return to the first shape from the second shape (i.e., the spring member expands from the compressed state). The moving body is thus urged towards the side at which the communication port inside the main container is provided.

A hemostatic instrument of this application includes a band body wound and fixed around a region of a limb in which bleeding is to be stopped, an expansion member connected to the band body and expanded when a fluid is injected to apply a pressure force for stopping bleeding in the region to the region, a connector provided in an end portion of an injection passage for injecting the fluid into the expansion member, and a pressure adjustment unit that adjusts a pressure of the expansion member. The pressure adjustment unit includes a main container portion connected to communicate with the expansion member. The main container portion has a fluid passing hole for extracting a portion of the fluid. The pressure adjustment unit also includes a sliding member installed in (e.g., mounted on) the main container portion and movable along the main container portion from a state in which the fluid passing hole of the main container portion is blocked to a position to open the fluid passing hole. The pressure adjustment unit includes a moving body movable inside the main container portion between a position at which the fluid passing hole is blocked and a position at which the fluid passing hole is not blocked. The main container portion includes a communication port for communication with the expansion member, and a force applying means that applies a force that directs the moving body to a side at which the communication port is provided.

The force applying means applies a force to the moving body inside the main container portion to direct the moving body to the communication port side. For this reason, when the operator opens the fluid passing hole of the main container portion to reduce an internal pressure inside the expansion member, an internal pressure of a space formed between the moving body inside the main container portion and the communication port is reduced. The moving body thus moves toward the communication port side by the force applying means. The moving body inside the main container portion moves to the other end portion side of the main container portion until the opened fluid passing hole is blocked. Therefore, the operator may open the fluid passing hole of the main container portion to release a portion of the fluid of the expansion member by simply sliding the sliding member with respect to the main container portion and may adjust the pressure force exerted by the expansion member and applied to the region in which bleeding is to be stopped. This configuration allows the operator to easily adjust the pressure force applied to the region in which bleeding is to be stopped in response to a state of the patient. The effort of the operator to adjust the pressure force may be reduced.

In this specification, the "fluid" includes liquid in addition to gas.

The "force applying means" may be a means for applying a force for directing the moving body to the communication port side inside the main container portion. For example, the force applying means may be a means that connects the moving body to the main container portion to apply a force to the moving body using an elastic force, and the like or may be a means that applies a force to the moving body using a magnetic force, and the like in a state in which the moving body is not connected to the main container portion.

The force applying means may correspond to a first magnet and a second magnet in one embodiment. The first magnet is disposed in the main container portion, and the second magnet is disposed in the moving body. The force applying means thus may apply a force to the moving body to direct the moving body to a side at which the communication port is provided using the magnetic force (i.e., the repulsive force) acting between the first magnet and the second magnet.

A repulsive force acts between the first magnet and the second magnet. The main container portion has one end portion and an other end portion opposite to the one end portion. The communication port for communication with the expansion member is provided in the other end portion, and the first magnet is provided in the one end portion. A repulsive force acts between the first magnet and the second magnet. In this way, a force at which a space (first space) formed between the moving body inside the main container and the one end portion of the main container portion acts on the moving body (a force at which the force applying means acts on the moving body) may be set by the repulsive force acting between the first magnet and the second magnet. It is thus possible to have a configuration in which no more load than necessary to inject the fluid into the expansion member is applied when the operator expands the expansion member.

The hemostatic instrument is not restricted to the above-described embodiment, and may be variously modified within the scope not departing from the scope of claims.

Some of the respective components of the embodiment may be omitted, and the respective components may be arbitrarily combined differently from the above description.

For example, the fluid injected into the balloon 5 and the auxiliary balloon 6 is not restricted to air. Examples of the fluid may include nitrogen or another gas. In addition, the fluid is not restricted to a gas, and the fluid may be a liquid such as water or a normal saline solution.

In the illustrated embodiment, four air passing holes or three air passing holes are described as the fluid passing hole configurations. However, the invention is not limited to any specific number of holes, and the number of air passing holes may be arbitrarily set. The pressure adjustment unit is connected through the injection portion 50. However, it is possible to employ a configuration in which the pressure adjustment unit is directly connected to the balloon 5 and the auxiliary balloon 6 to reduce air (fluid) inside the balloon 5 and the auxiliary balloon 6.

The detailed description above describes a hemostatic instrument and a method of using the hemostatic instrument. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic instrument comprising:
   a band body configured to be wound and fixed around a region of a limb at which bleeding is to be stopped;
   an expansion member connected to the band body and possessing an interior, the expansion member being configured to expand when a fluid is injected into the interior of the expansion member to apply a pressure force to the region of the limb for stopping the bleeding in the region of the limb;
   a connector provided at an end portion of an injection passage for injecting the fluid into the expansion member; and
   a pressure adjustment unit configured to adjust a pressure of the expansion member that is applied to the region of the limb, the pressure adjustment unit including:
      a main container portion comprising a communication port that is connected to and communicates with the interior of the expansion member, the communication port being at one end of the main container portion, the main container portion including a fluid passing hole configured to allow a portion of the fluid in the expansion portion to be released to an outside environment,
      a sliding member mounted on the main container portion, the sliding member being movable along the main container portion from a closed position blocking the fluid passing hole of the main container portion to an open position that allows the portion of the fluid in the expansion member to be released through the fluid passing hole to the outside environment, and
      a moving body positioned within the main container portion, the moving body being movable within the main container portion between a first position at which the moving body blocks the fluid passing hole so that fluid in the main container portion is blocked from passing through the fluid passing hole and a second position at which the moving body does not block the fluid passing hole so that the fluid passing hole is open and fluid in the main container portion passes through the fluid passing hole;
   the main container portion of the pressure adjustment unit including a force applying means for applying a force to urge the moving body within the main container portion towards the one side at which the communication port is provided.

2. The hemostatic instrument according to claim 1, wherein
   the force applying means is a first magnet and a second magnet,
   the first magnet is disposed in the main container portion, and
   the second magnet is disposed in the moving body.

3. The hemostatic instrument according to claim 2, wherein a repulsive force acts between the first magnet and the second magnet to urge the second magnet away from the first magnet.

4. The hemostatic instrument according to claim 3, wherein
the first magnet possesses a proximal end and a distal end, the distal end of the first magnet possessing a first pole,
the second magnet possesses a proximal end and a distal end, the proximal end of the second magnet possessing a second pole, and
the first pole of the first magnet and the second pole of the second magnet possessing the same polarity.

5. The hemostatic instrument according to claim 1, wherein the force applying means is a spring positioned to apply a biasing force on the moving body to urge the moving body towards the one side where the communication port is provided.

6. The hemostatic instrument according claim 1, wherein
the main container portion has one end portion and an other end portion, and
the one end portion and the other end portion have retaining inhibition portions that inhibit the sliding member from moving beyond the retaining inhibition portions of the main container portion.

7. The hemostatic instrument according to claim 1, comprising a rigid plate provided within the band body, the rigid plate including a curved portion, the rigid plate being more rigid than the band body.

8. The hemostatic instrument according to claim 7, wherein the curved portion of the rigid plate contacts and applies a force to the expansion member so that the expansion member applies the pressure force to the region of the limb for stopping the bleeding in the region of the limb when the expansion member is expanded.

9. A hemostatic instrument comprising:
a flexible band configured to be wound around a region of a limb of a living body that includes a bleeding puncture site;
an inflatable member provided on an inner peripheral side of the flexible band that will face toward the limb during use of the hemostatic instrument, the inflatable member being configured to expand when fluid is injected into an interior of the inflatable member, the inflatable member being positioned to apply a pressure force to the region of the limb to stop the bleeding of the puncture site in the region of the limb when the inflatable member is expanded;
an injection tube possessing a distal end and a proximal end, the distal end of the injection tube being connected to the inflatable member, the injection tube allowing the fluid to flow into the inflatable member;
a first connector possessing a distal end and a proximal end, the distal end of the connector communicating with the injection tube and the inflatable member, the proximal end of the connector being configured to connect to a fluid injection device to introduce fluid into the injection tube and into the inflatable member; and
a pressure adjustment unit connected to the injection tube, the pressure adjustment unit communicating with the injection tube and the inflatable member;
the pressure adjustment unit including:
a main container portion possessing an interior and an outer circumferential surface, the main container portion comprising a plurality of through holes communicating the interior of the main container portion with the outside environment to allow a portion of the fluid in the inflatable portion to be released to the outside environment by way of the main container portion, the main container portion also comprising a communication port opening into the interior of the main communication portion and communicating with the interior of the inflatable member by way of the injection tube,
a sliding member mounted on the outer circumferential surface of the main container portion, the sliding member being movable relative to the main container portion from a closed position in which the sliding member covers all of the through holes to a first open position in which one of the through holes is not covered by the sliding member to allow the portion of the fluid in the inflatable portion to be released through the one through hole to the outside environment, and
a movable body positioned in the interior of the main container portion, the movable body being positionable in one position in which the movable body is spaced from all of the through holes so that the movable body does not axially overlap any of the through holes, the movable body being movable from the one position to an other position in which the movable body axially overlaps one of the through holes to prevent fluid in the interior of the main container body to flow through the one through hole to the outside environment.

10. The hemostatic instrument according to claim 9, wherein
the main container portion of the pressure adjustment unit comprises a first magnet at one end of the main container portion,
the movable body comprises a second magnet that is fixed to the movable body so that the movable body and the second magnet move together, and
the first magnet applies a force on the second magnet that urges the movable body axially away from the one end of the main container portion.

11. The hemostatic instrument according to claim 9, wherein
the main container portion of the pressure adjustment unit comprises a biasing spring at one end of the main container portion, and
the biasing spring applies a force to the movable body to urge the movable body away from the one end of the main container portion.

12. The hemostatic instrument according to claim 9, comprising a rigid plate provided within the band body, the rigid plate including a curved portion, the rigid plate being more rigid than the band body.

13. The hemostatic instrument according to claim 12, wherein the inflatable body is offset from a center of the rigid plate towards the curved portion of the rigid plate in a longitudinal direction of the band body.

14. A method comprising:
attaching a hemostatic instrument to a puncture site of a limb of a living body, the hemostatic instrument comprising a band and an inflatable body, the inflatable body possessing an interior, the attaching of the hemostatic instrument to the puncture site of the limb of the living body comprising winding the band around the limb of the living body so that the inflatable body is positioned between the band and the puncture site;
injecting a fluid into the interior of the inflatable body after the attaching of the hemostatic instrument to the puncture site of the limb to expand the inflatable body and apply pressure to the puncture site of the limb to assist in stopping bleeding, the interior of the inflatable body being in fluid communication with an interior of a main body, the main body including a plurality of through holes communicating the interior of the main body with the outside environment, the main body including a sliding member mounted on the main body and a movable member movably positioned in the interior of the main body;

reducing pressure within the inflatable body by moving the sliding member relative to the main body from a position in which the sliding member covers all of the through holes to a position in which one of the through holes is not covered by the sliding member and while the movable member is spaced from the one through hole so that fluid in the interior of the main body flows through the one through hole to the outside environment; and automatically moving the movable member in the interior of the main body after reducing the pressure within the interior of the inflatable body so that the movable member blocks the one through hole.

15. The method according to claim 14, wherein the automatically moving of the movable member in the interior of the main body after reducing the pressure within the interior of the inflatable body includes applying a force to the movable member that causes the movable member to automatically moving when the pressure in the interior of the inflatable body decreases to a predetermined pressure.

16. The method according to claim 14, further comprising, after automatically moving the movable member to block the one through hole:

further reducing the pressure within the inflatable body by moving the sliding member relative to the main body to uncover an other through hole of the plurality of through holes and while the movable member is spaced from the other through hole so that fluid in the interior of the main body flows through the other through hole to the outside environment; and automatically moving the movable member in the interior of the main body after further reducing the pressure within the interior of the inflatable body so that the movable member blocks the first through hole and the other through hole.

17. The method according to claim 16, further comprising, after automatically moving the movable member to block the first through hole and the other through hole:

still further reducing the pressure within the inflatable body by moving the sliding member relative to the main body to uncover an additional through hole of the plurality of through holes and while the movable member is spaced from the additional through hole so that fluid in the interior of the main body flows through the additional through hole to the outside environment; and automatically moving the movable member in the interior of the main body after still further reducing the pressure within the interior of the inflatable body so that the movable member blocks the additional through hole.

18. The method according to claim 14, wherein the main body includes first and second opposite ends, the plurality of through holes includes a first through hole located closer to the first end of the main body than all others of the through holes, and the plurality of through holes includes a second through hole located closer to the second end of the main body than all others of the through holes, the interior of the inflatable body being in fluid communication with the interior of the main body by way of a tube that opens into the interior of the main body at a position between the second end of the main body and the second through hole;

the method further comprising:

the movable member being positioned between the first end of the main body and the first through hole so that the first through hole is not blocked by the movable member before the reducing of the pressure within the inflatable body.

19. The method according to claim 14, wherein the interior of the inflatable body is in fluid communication with the interior of the main body by way of a first tube that includes one end connected to the inflatable body and an other end connected to a bag body, and a second tube that includes one end connected to the bag body and an other end connected to the main body, and wherein the injecting of the fluid into the interior of the inflatable body includes injecting the fluid into the bag body so that the fluid flows into the interior of the inflatable body by way of the first tube.

* * * * *